United States Patent [19]
Dobler et al.

[11] Patent Number: 5,985,821
[45] Date of Patent: Nov. 16, 1999

[54] FRAGRANCE GEL PRODUCT

[75] Inventors: Sven Dobler, New York, N.Y.;
Suzanne Diller, Los Angeles, Calif.

[73] Assignee: Orlandi, Inc., Farmingdale, N.Y.

[21] Appl. No.: 09/140,915

[22] Filed: Aug. 27, 1998

Related U.S. Application Data

[60] Provisional application No. 60/057,126, Aug. 28, 1997.

[51] Int. Cl.$^6$ .............................. A61K 7/46; A61L 9/015
[52] U.S. Cl. .................................. 512/2; 512/4; 424/76.2
[58] Field of Search ........................... 512/2, 4; 252/522; 424/76.2

[56] References Cited

U.S. PATENT DOCUMENTS

| | | | |
|---|---|---|---|
| 4,067,824 | 1/1978 | Teng et al. | 252/522 |
| 4,089,814 | 5/1978 | Schmolka | 252/522 |
| 4,128,507 | 12/1978 | Mitzner | 252/522 |
| 4,617,147 | 10/1986 | Shibanai | 252/522 |
| 4,719,040 | 1/1988 | Traas et al. | 512/4 |
| 4,809,912 | 3/1989 | Santini | 239/60 |
| 5,391,420 | 2/1995 | Bootman et al. | 428/195 |
| 5,643,866 | 7/1997 | Ansari et al. | 512/4 |
| 5,833,998 | 11/1998 | Biedermann et al. | 424/401 |

*Primary Examiner*—C. H. Kelly
*Assistant Examiner*—Monique T. Cole
*Attorney, Agent, or Firm*—Paul M. Denk

[57] ABSTRACT

A fragrance is supplied in a gel form. The fragrance includes a fragrance oil, alcohol, and a sufficient amount of polymer to increase the viscosity of the oil and alcohol to the point where it will not readily pour from a container.

1 Claim, No Drawings

FRAGRANCE GEL PRODUCT

CROSS-REFERENCE TO RELATED APPLICATIONS

This application is related to Provisional Application Ser. No. 60/057,126, filed Aug. 28, 1997, and which is incorporated herein by reference.

BACKGROUND OF THE INVENTION

This invention relates generally to the concept of providing a fragrance that is blended with polymers in order to thicken the viscosity of the material into a gel form, that can be easily dispensed from a bottle, through a pump actuator, as a roll-on product, or from a packet structure, for applying a fragrance to the person.

Fragrances have been used and applied for the purpose of enhancing personal aroma from the days of the Romans, if not earlier. Today, fragrance oil is mixed with alcohol, and some water, to produce what is generally referred to as toilet water, and the like. Such is sold in bottles with a spray actuator pump or in a bottle as a splash applied product. In both cases, the dispensing of the product is difficult to control. Especially, with spray application mechanisms, sometimes only a little and frequently too much of the fragrance is undesirably dispensed.

To the inventor's knowledge, the only fragranced gel products that have been marketed, to date, are generally for use for hair styling and for sustaining hair coiffures once set. Such gels, as is normally known, usually feel "greasy" to the touch, and do not absorb easily into the skin, once applied. Such type gels are not designed nor or they meant to be used as a personal fragrance.

There are other types of wet fragrance liquid form of sampling products, or carrying vehicles, that are used in the marketplace today, as a means for sampling of perfumes, toilet water, and the like. Scent seals are available, and are pressure sensitive type of labels that incorporate a wet fragrance formulation. This is used only for sampling purposes, and has no retail application. Vials of pure fragrance toilet water, in glass containers, are available, but these exhibit some of the "uncontrolled" dispensing problems normally associated with the less viscous liquid type of applications. The True Scent type of capsules, that are also available in the art, are large gelatin type capsules containing pure fragrance inside of them. These types of capsules also have problems with dispensing, and have little or no retail application for personal usage.

SUMMARY OF THE INVENTION

It is the principal object of this invention to provide a gel form of fragrance that may be dispensed for retail or for sampling purposes, in packets or other containers, or for direct application during normal usage.

The gel fragrance material of the current invention is designed to allow for a controlled dispensing of any of the infinite number of fragrances available upon the market. The gel can be filled into packets for samples or into bottles or pumps for retail use. The fragrance can be gently squeezed out of the container in just the right dosage, without spilling, for application to the skin. There is enough content of the gel material to be applied at all of the various pulse points or for multiple applications, as fragrances and perfumes are normally applied during standard usage. The packets of this current invention are ideal for in store or direct mail sampling, or as a gift for use for over-night trips, purses, gym bags, or for any time the need for such an actual perfume product is required, but when conveying the same within a bottle is inconvenient and impractical.

With the novel gel formulation of this invention, the fragrance, as applied, does not spill, splash, or spray out of the bottle, or its packet, and the gel can be easily squeezed out of its bottle, with a pump, or it may be dispensed from a packet sampler, in a very controlled manner. The gel composition as formulated is not greasy, and easily absorbs into the skin, without leaving any sticky feeling.

In addition, since the formulated fragrance of the packet of this invention is easily absorbed into the skin, such can be achieved without leaving any stains, or a creamy or overly moist surface, once applied.

Hence, it is a principal object of this invention to provide a gel form of dispensing means that can contain fragrance oil, and be used either for sampler purposes, or for direct application during standard usage.

Another object of this invention is to provide a very controlled amount of a fragrance gel that may be sampled or packaged for application.

Still another object of this invention is to provide a gel-like formulation for containing or absorbing a fragrance, of any one of the multitude of perfume manufacturers, for use either for sampling or personal application.

Still another object of this invention is to provide a gel formulation for holding a fragrance that will not spill, splash, or spray out of its bottle or container, once applied.

Yet another object of this invention is to provide a fragrance gel that is not greasy, and can easily be absorbed into the skin, without leaving any sticky or moist feeling.

Still another object of this invention is to utilize the fragrance gel of this application as a water-resistant composition ideal for sports or athletic applications.

These and other objects will become more apparent to those skilled in the art upon reviewing the summary of this invention, and upon undertaking a study of the description of its preferred embodiment.

DESCRIPTION OF THE PREFERRED EMBODIMENT

This invention contemplates the formation of a heavier viscous form of gel, that may be doctored or treated with any of a variety of fragrances, perfumes, toilet water, or the like, for the purpose of providing a new and novel means for application of fragrances to the person, or for sampling purposes.

The formulation for this particular gel, to which the fragrance or fragrance oil may be applied, includes denatured alcohol, and either organic or inorganic polymers or a combination of such polymers, to add to the viscosity of the composition, and to allow for the absorption of the fragrance oil therein, once mixed.

Examples of such polymers are as follows:

| | | |
|---|---|---|
| Acrylamides Copolymer | Benzoic Acid/Phthalic Anhyride/Pentaerythritol/Neopently Glycol/Palmitic Acid Copolymer | Dodecanedioic Acid/Cetearyl Alcohol/Glycol Copolymer |
| Acrylamide/Sodium Acrylate Copolymer | | Ethylene/Acrylate Copolymer |
| Acrylate/Acrylamide Copolymer | Butadiene/Acrylonitrile Copolymer | Ethylene/Maleic Anhydride Copolymer |
| Acrylate/Ammonium Methacrylate Copolymer | Butylated Urea-Formaldehyde Resin | Ethylene/Vinyl Acetate Copolymer |
| Acrylates Copolymer | Butly Benzoic Acid/Phthalic Anhydride/Trimethyiolethane Copolymer | Ethyl Ester of PVM/MA Copolymer |
| Acrylates/Diacetoneacrylamide Copolymer | | Hexadimethrine Chloride |
| Acrylates/Steareth-20 Methacrylate Copolymer | Butyl Ester of Ethylene/Maleic Anhydride Copolymer | Hydrogenated C6–14 Olefin Polymers |
| Acrylic/Acrylate Copolymer | | Hydrogenated Polyisobutene |
| Adipic Acid/Dimethylaminohydroxypropyl Diethylenetriamine Copolymer | Butyl Ester of PVM/MA Copolymer | Hydroxyethyl PEI-1000 |
| | Calcium/Sodium PVM/MA Copolymer | Hydroxyethyl PEI-1500 |
| Adipic Acid/Epoxypropyl Diethylenetriamine Copolymer | Carbomer 910 | Isobutylene/Isoprene Copolymer |
| | Carbomer 934 | Isobutylene/Maleic Anhydride Copolymer |
| Allyl Stearate/VA Copolymer | Carbomer 934P | Isopropyl Ester of PVM/MA Copolymer |
| Aminoethylacrylate Phosphate/Acrylate Copolymer | Carbomer 940 | Melamine/Formaldehyde Resin |
| | Carbomer 941 | Methacryloyl Ethyl Betaine/Methacrylates Copolymer |
| Ammonium Acrylates Copolymer | Corn Starch/Acrylamide/Sodium Acrylate Copolymer | |
| Ammonium Styrene/Acrylate Copolymer | | Methoxy PEG-22/Dodecyl Glycol Copolymer |
| Ammonium Vinyl Acetate/Acrylates Copolymer | DEA-Styrene/Acrylates/Divinylbenzene Copolymer | Methylstyrene/Vinyltoluene Copolymer |
| AMP Acrylates/Diacetoneacrylamide Copolymer | | Nylon |
| AMPD Acrylates/Diacetoneacrylamide Copolymer | Diethylene Glycolamine/Epichlorohydrin/Piperazine Copolymer | Nylon-12 |
| | | Sodium Polymethacrylate |
| Octadecene/Maleic Anhydride Copolymer | Polyquaternium-4 | Sodium Polynaphthalene Sulfonate |
| Octylacrylamide/Acrylates/Butylaminoethyl Methacrylate Copolymer | Polyquaternium-5 | Sodium Polystyrene Sulfonate |
| | Polyquaternium-6 | Sodium Styrene/Acrylate/PEG-10 Dimaleate Copolymer |
| Octylacrylamide/Acrylates Copolymer | Polyquaternium-7 | |
| Oxidized Polyethylene | Polyquaternium-8 | Sodium Styrene/Acrylates/Divinylbenzene Copolymer |
| PEG-22/Dodecyl Glycol Copolymer | Polyquaternium-9 | |
| PEG-45/Dodecyl Glycol Copolymer | Polyquaternium-10 | Sodium Styrene/PEG-10 Maleate/Nonoxynol-10 Maleate/Acrylate Copolymer |
| PEI-7 | Polyquaternium-11 | |
| PEI-15 | Polyquaternium-12 | Starch/Acrylates/Acrylamide Copolymer |
| PEI-30 | Polyquaternium-13 | Stearyvinyl Ether/Maleic Anhydride Copolymer |
| PEI-45 | Polyquaternium-14 | Styrene/Acrylamide Copolymer |
| PEI-275 | Polyquaternium-15 | Styrene/Acrylate/Acrylonitrile Copolymer |
| PEI-700 | Polystyrene | Styrene/Acrylate/Ammonium Methacrylate Copolymer |
| PEI-1000 | Polyvinyl Acetete | |
| PEI-1500 | Polyvinyl Alcohol | Styrene/Acrylate Copolymer |
| PEI-2500 | Polyvinyl Butyral | Styrene/Maleic Anhydride Copolymer |
| Phthalic Anhydride/Glycerin/Glycidyl Decanoate Copolymer | Polyvinyl Imidazolinium Acetate | Styrene/PVP Copolymer |
| | Polyvinyl Laurate | Sucrose Benzoate/Sucrose Acetate Isobutyrate/Bytyl Benzyl Phthalate Copolymer |
| Phthalic/Trimelitic/Glycols Copolymer | Polyvinyl Methyl Ether | |
| Polyacrylamide | Potassium Aluminum Polyacrylate | Sucrose Benzoate/Sucrose Acetate Isobutyrate/Butyl Benzyl Phthalate/Methyl Methcrylate Copolymer |
| Polyacrylamidomethylpropane Sulfonic Acid | PVM/MA Copolymer | |
| Polyacrylic Acid | PVP | |
| Polyaminopropyl Biguanide | PVP/Dimethylaminoethylmethacrylate Copolymer | Sucrose Benzoate/Sucrose Acetate Isobutyrate Copolymer |
| Polyamino Sugar Condensate | | |
| Polybutene | PVP/Eicosene Copolymer | Toluenusulfonamide/Formaldehyde Resin |
| Polybutylene Terephthalate | PVP/Ethyl Methacrylate/Methacrylic Acid Copolymer | Urea/Formaldehyde Resin |
| Polychlorotrifluoroethylene | | Urea/Melamine/Formaldehyde Resin |
| Polydipentene | PVP/Hexadecene Copolymer | Vinyl Acetate/Crotonates Copolymer |
| Polyethylacrylate | PVP-Iodine | Vinyl Acetate/Crotonic Acid Copolymer |
| Polyethylene | PVP/VA Copolymer | Vinyl Acetate/Crotonic Acid/Methacryloxybenzophenone-1 Copolymer |
| Polyisobutene | PVP/Vinyl Acetate/Itaconic Acid Copolymer | |
| Polyisoprene | Rayon | |
| Polyquaternium-1 | Sodium Acrylate/Vinyl Alcohol Copolymer | Vinyl Acetate/Crotonic Acid/Vinyl Neodecanoate Copolymer |
| Polyquaternium-2 | Sodium C4–12 Olefin/Maleic Acid Copolymer | |

The packets in which the gel may be applied, if it is dispensed in single dosage applications, may be formed of any type of standard industry laminated packet structures, such as polyethylene film, or the structures including but not limited to polyester, saran, sirlin, barex, foil, polyethylene or the like, that may be heat sealed around their edges, and have a quantity of the gel applied thereto, for sampling purposes. Or, such gel packets can be used for single dosage applications, and be sold in that manner, to supply just the efficient amount of fragrance type of gel, of this invention, to the user, once opened. On the other hand, the formulation of this invention, containing its fragrance oil, can be applied into glass bottle form, into pumps, or into squeeze bottles that dispense upon applying pressure to the sides of the vessel, to obtain just the right amount of dispensed fragrance, within the gel, for immediate application to the various body parts to which perfumes are normally applied.

The fragrance gel of this invention can be packaged within the packets, for hand-out purposes, or even for direct mail sampling, in order to help stimulate the sales of particular perfumes, that may be marketed at the retail outlets. The gel can also be packaged in retail bottles, and can be sold directly as perfume products, by any other variety of well-known marketing methods, whether it be by mail-order, catalog, or from the retail store.

The fragrance oil components of this composition are normally added to the gel composition in an amount from approximately 10% to 20% by weight of the completely formulated product.

In addition, the fragrance packets of this invention may be printed as in standard industry flexographic or rotogravure equipment. Print is either applied to the surface of the structure with a varnish overcoat to protect against scuffing or color fading of the samples, or the print can be "burned" within the laminate structure.

The fragrance gel includes (by weight) about 10–20% fragrance oils, about 80–85% denatured alcohol, and about 5% polymer. The polymer can be any organic or inorganic, synthetic or natural polymer, and is used to increase the viscosity of the formulation.

Variations or modifications to the formulation of this invention, and other types of ingredients that may add to the texture, coloration, or even degrees of viscosity to the gel, may be considered by those skilled in the art upon reviewing this description of the invention as provided herein. Such variations or modifications are intended to be encompassed within the scope of the invention as analyzed and described herein. The specific ingredients as listed, for the formulation as provided, is done so for illustrative purposes only.

We claim:

1. A spreadable fragrance gel consisting essentially of, by weight, about 10–20% fragrance oil, about 80–85% alcohol, and about 5% polymer to increase the viscosity of the oil and alcohol to the point where it will not readily pour from a bottle but remains spreadable.

* * * * *